United States Patent [19]

Michaud et al.

[11] 4,069,383
[45] Jan. 17, 1978

[54] METHOD OF PREPARING MELAMINE FROM CYANAMIDE AND/OR DICYANDIAMIDE

[75] Inventors: Horst Michaud; Günter Ortenburger; Wilhelm Poschinger; Heinrich Röck; Josef Seeholzer, all of Trostberg, Germany

[73] Assignee: Suddeutsche Kalkstickstoff-Werke Aktiengesellschaft, Trostberg, Germany

[21] Appl. No.: 715,027

[22] Filed: Aug. 17, 1976

[30] Foreign Application Priority Data

Aug. 18, 1975  Germany .............................. 2536689

[51] Int. Cl.$^2$ .......................................... C07D 251/58
[52] U.S. Cl. .................................................. 544/202
[58] Field of Search ................................ 260/249.7 C

[56] References Cited

U.S. PATENT DOCUMENTS 3,257,169   6/1966   Sprague ........................ 260/249.7 C Primary Examiner—John M. Ford
Attorney, Agent, or Firm—Burgess, Dinklage & Sprung

[57] ABSTRACT

Melamine is prepared from cyanamide and/or dicyandiamide by contacting the cyanamide and/or dicyandiamide at approximately atmospheric pressure in an organic solvent at 100° to 250° C with at least one solvent selected from the group having the formulas

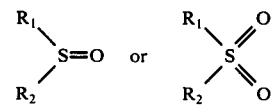

wherein
R$_1$ and R$_2$ are alkyl which may be joined together to form an alkylene ring, in the simultaneous presence of alkali hydroxide or alkaline earth hydroxide.

14 Claims, No Drawings

METHOD OF PREPARING MELAMINE FROM CYANAMIDE AND/OR DICYANDIAMIDE

The invention relates to a process for the preparation of melamine from cyanamide and/or dicyandiamide at approximately atmospheric pressure.

Processes for the preparation of melamine on the basis of lime, charcoal and electrical energy with calcium carbide and calcium cyanamide as intermediates are again acquiring importance as a result of changes in the raw materials situation.

The process heretofore performed on a large technical scale for the preparation of melamine from calcium cyanamide is a multi-step process: by the hydrolysis of the calcium cyanamide, first cyanamide is formed, which is transformed to dicyandiamide and isolated. After drying in high-pressure autoclaves at 200 atmospheres and about 300° C, the dicyandiamide is reacted to form melamine in an approximately 95% yield. A recrystallization of the crude melamine from water is then necessary. Since the solubility of the melamine at 90° C is only about 4%, large amounts of water and therefore large amounts of energy are required for the purification of the melamine.

To avoid the high pressures of the known process, attempts have been made to perform the reaction of the dicyandiamide to melamine in appropriate solvents. In particular, methanol and isobutanol have been proposed for this purpose (Ullmann, Vol. 12, pp. 281-282 (1960). Due to the necessary presence of ammonia and a minimum temperature of 160° C, relatively high pressures are still necessary, but the melamine yield has amounted to no more than 80%.

In U.S. Pat. No. 2,206,005 the pressure-less production of melamine from dicyandiamide in benzyl alcohol as solvent is described. By this process, again, melamine yields of less than 80% are obtained, since large amounts of ammeline and ammelide are formed as by-products.

In the process of German Pat. No. 933,866, cyanamide and/or dicyandiamide, in crystalline form or dissolved in an organic solvent, are placed in relatively large amounts of an indifferent liquid such as tetrahydronaphthaline, diphenyl ether, or higher saturated aliphatic hydrocarbons, preferably at 190° to 250° C, under normal pressure. The melamine produced in this case is no more than 95% pure, since it is contaminated by deamination products which have also formed with a yielding of ammonia, and this necessitates recrystallization.

The process proposed in German Pat. No. 955,952 for the preparation of melamine by the atomization of an aqueous solution of cyanamide and/or dicyandiamide in a hot gas stream serving as a heat carrier and heat buffer, at temperatures between 275° and 300° C, requires such great amounts of energy for the evaporation of all of the water that this fact alone makes the process very uneconomical; in addition, the product that results contains greater contents of impurities, which again requires recrystallization.

All of the processes described in the literature, which were aimed at an improvement of the preparation of melamine from calcium cyanamide, have failed to supplant the traditional high-pressure processes, especially for economical reasons, and consequently they have not found acceptance in the art.

The invention is therefore addressed to the problem of developing a process for the preparation of melamine, which, setting out from crystalline or water-dissolved cynamide and/or dicyandiamide, and operating at approximately atmospheric pressure in a suitable solvent, will directly yield melamine of high purity in a high yield.

This problem is solved by the invention in that the reaction of dicyandiamide and/or cyanamide in at least one solvent of the general formula

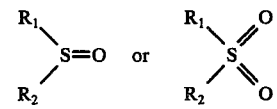

wherein $R_1$ and $R_2$ represent alkyl groups, which can be identical or different and together can also form a ring is performed in the simultaneous presence of alkali hydroxide or alkaline earth hydroxide. Dimethylsulfoxide is preferred as the organic solvent, and potassium hydroxide or sodium hydroxide is preferred as the alkali hydroxide. The yields which can be achieved in the transformation of cyanamide and/or dicyandiamide in the abovespecified system of organic solvent plus alkali hydroxide or alkaline earth hydroxide amount to as much as 97% of a melamine of a purity exceeding 99.5%. The melamine thus obtained can, after separation of the solvent, be used without further purifying operations for such processes as the condensation reaction with formaldehyde. The total malamine yield amounts, in the continuously performed method, to more than 98% with respect to the cyanamide or dicyandiamide starting substances.

The moieties $R_1$ and $R_2$ in the compounds of the General Formula

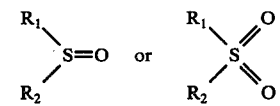

can best contain from 1 to 10, preferably 1 to 4, carbon atoms, e.g., methyl, ethyl, propyl or butyl groups, $R_1$ and $R_2$ being able to be identical or different or also to form a ring with one another. Typical representatives of these suitable solvents are compounds such as dimethyl sulfoxide, diethylsulfoxide, dimethylsulfone, diethylsulfone or sulfolan. Especially suitable as reaction media are those compounds which are liquid at room temperature and have a boiling point of about 150° to 250° C. For the adjustment of the appropriate melting and boiling points, mixtures of the above-named solvents can also be used, or the reaction is performed at reduced or elevated pressure.

In order for the reaction to produce and especially pure melamine in a high yield, the presence of alkali hydroxide or alkaline earth hydroxide is required. Any of the alkali hydroxides can be used, such as lithium, sodium, potassium or cesium hydroxide, or any sufficiently basic alkaline earth hydroxide, such as calcium, strontium or barium hydroxide, as pure compounds, or in a mixture of the alkali or alkaline earth hydroxides together. Without these compounds to act as catalysts, either no melamine or only traces of melamine are formed. For the achievement of an optimum yield and purity in the melamine, certain amounts of the named alkali or alkaline earth hydroxides must be used, less catalytically active base being required for the reaction of cyanamide to melamine than in the reaction of dicyandiamide to melamine. For example, if dicyandiamide is to be used with potassium hydroxide, 0.1 to 0.2 mole of potassium hydroxide is used per mole of dicyandiamide, whereas if cyanamide is used as the starting product, only 0.02 to 0.05 mole of potassium hydroxide is used per mole of cyanamide. Slightly higher amounts of catalytically acting base are desirable, namely 0.05 to 0.5 mole, if, instead of alkali hydroxide, alkaline earth hydroxides, preferably calcium or barium hydroxide, are used.

The transformation of dicyandiamide or cyanamide to melamine begins in the above-described system at a temperature as low as about 100° C. Higher temperatures are necessary for a rapid reaction. At temperatures of about 180° C the reaction is completed in 10 to 30 minutes. Under such reaction conditions the pressure in the apparatus can increase also to higher values of atmospheric pressure, such as, for example, to from 3 to 5 atmospheres absolute. On the other hand, operation in a slight vacuum of, for example, up to 100 Torr, will produce a melamine in a high yield. Instead of dicyandiamide, the reaction can be performed with cyanamide or mixtures of dicyandiamide and cyanamide. The transformation of cyanamide to melamine has proven especially advantageous. The consumption of alkali is lower than when dicyandiamide is used as the starting substance. It is furthermore possible to work with an aqueous cyanamide solution and thus to arrive directly at the crystalline melamine from the aqueous cyanamide solution produced by the hydrolysis of the calcium cyanamide, after concentrating the said solution to a content of 50 to 80% cyanamide, without the isolation of a solid intermediate product. The highly exothermic reaction of the trimerization of the cyanamide to melamine suffices to vaporize the water from the cyanamide solution and to maintain the desired reaction temperature. Surprisingly, in spite of the presence of water, neither ammeline nor ammelide are formed under the above-described reaction conditions. The melamine produced primarily from the solution is so pure that it does not need to be recrystallized for further processing.

When crystalline cyanamide or dicyandiamide are used, the following procedure is recommendable: the cyanamide or dicyandiamide are dissolved cold in the solvent in question, or made into a mash therein, and placed into a mixture, heated to the reaction temperature, of alkali or alkaline earth hydroxide in the same solvent, containing a trace of cyanamide or dicyandiamide. Then the mixture is allowed to react for 10 to 30 minutes thereafter, at the chosen reaction temperature. The small amount of cyanamide or dicyandiamide previously present brings about a thermal stabilization of the solvent.

When operating with aqueous cyanamide solution, we poured this solution preferably into the mixture of alkali hydroxide or alkaline earth hydroxide and solvent, which had a temperature of about 180° C and which likewise contained a small amount of cyanamide or dicyandiamide for stabilization, at such a rate that the reaction temperature was maintained. The water escaping in vapor form was withdrawn.

The melamine forming under the conditions of the reaction precipitates in crystalline form upon cooling. It is separated, e.g., by filtration or centrifugation, and then either suspended in water and again filtered, or washed with water in the centrifuge. The product thus obtained is entirely colorless and has a melamine content of over 99.5%; it is not only free of hydrolysis products such as ammeline and ammelide, but also of colored deamination products such as melem, melam or melon, and it is an immediately salable product, since it can be used without further refining operations for condensation reactions and hence for the production of melamine resin.

In the continuous procedure, the small amount of melamine remaining in the mother liquor (about 3 to 5%) is not isolated, but is added to the next mixture. Since no concentration of impurities takes place, yields of over 97% of high-purity melamine are obtained in a plurality of successive batches; furthermore, the amount of alkali base or alkaline earth base required as catalyst is reduced.

The method of the invention for the preparation of melamine from calcium cyanamide or aqueous cyanamide solution represents an important technical advance in comparison with the methods formerly practiced and described, because
1. the preparation of the melamine is performed in a single-step reaction from cyanamide,
2. the isolation of solids as intermediates is unnecessary,
3. substantially lower temperatures are required, and in general it is sufficient to operate under approximately atmospheric pressure,
4. capital, labor and overhead costs are considerably reduced as a result of the single-step procedure it involves, and
5. high-purity melamine is obtained as the reaction product without recrystallization.

EXAMPLES

The following examples are intended to explain the process:

EXAMPLE 1

To a mixture heated rapidly to 180° C and composed of 80 g of dimethylsulfoxide, 6 g of powdered potassium hydroxide and 4 g of dicyandiamide, a solution of 60 g of dicyandiamide in 120 g of dimethylsulfoxide is added drop by drop over a period of 22 minutes, the reaction temperature being maintained at about 180° C. After the end of the reaction, the mixture is allowed to after-react for 5 more minutes at 180° C, and then it is cooled. While it is cooling, most of the melamine separates in crystalline form. The melamine is suction filtered, stirred up with water and again filtered. 50.8 g is obtained of pure, colorless melamine, corresponding to a yield of 79.4%. 8.25 g of melamine, or 12.8%, are still to be found in the filtrate. The overall yield of melamine thus amounts to 92.2%. 1.37 grams, or 2.1%, of unreacted dicyandiamide remains in the filtrate.

EXAMPLE 2

A solution of 63 g of solid cyanamide in 40 g of dimethylsulfoxide is added drop by drop over a period of 8 minutes to a mixture, heated at 180° C, of 100 g of dimethylsulfoxide, 4 g of potassium hydroxide and 1 g of cyanamide. After an additional 12 minutes of reaction time at 180° C, the mixture is cooled. The precipitated melamine is removed by filtration, suspended in water, and suction filtered. After drying, 56 g of melamine crystals are obtained, which corresponds to a yield of 87.7%. 2.5 grams, or 3.9%, of melamine still remain in the filtrate and wash water. The total yield, therefore, comes to 91.4%. 3.9% of diamide can furthermore still be detected in the filtrate.

EXAMPLE 3

A solution of 63 g of solid cyanamide in 40 g of sulfolan is added drop by drop over a period of 12 minutes to a mixture of 100 g of sulfolan and 4 g of potassium hydroxide, which is heated at 180° C. After a reaction time of 30 minutes at about 180° C, the mixture is cooled. The melamine that has crystallized is removed by filtration, stirred up in water, and suction filtered. After drying, 50 g of melamine is obtained, corresponding to a yield of 79.4%. 2.4 g, or 3.8%, of melamine still remains dissolved in the filtrate and wash water. The total yield thus amounts to 83.2% of melamine. 9.3% of unreacted dicyandiamide still remains in the filtrate.

EXAMPLE 4

A solution of 30 g of dicyandiamide and 30 g of solid cyanamide in 120 g of dimethylsulfoxide is added over a period of 11 minutes to a mixture, heated to 180° C, of 4.0 g of potassium hydroxide and 4.0 g of dicyandiamide in 80 g of dimethylsulfoxide. After an additional 5 minutes of reaction time at 180° C the mixture is cooled. The precipitated melamine is removed by filtration, stirred up in water, and again filtered. The first yield amounts to 53.8 g of melamine or 84.1%. As a second yield, an additional 5.7 g of 8.9% of melamine was found in the filtrate and wash water, so that the total yield amounted to 93.0%. An additional 1.43 g of 2.24% of unreacted dicyandiamide was detected.

EXAMPLE 5

113 g of dimethylsulfone is melted and heated to 100° C. 63 g of dicyandiamide and 5.6 g of powdered potassium hydroxide are added to the melt. The exothermic reaction raises the temperature of the mixture quickly to 210° C. After cooling to 60° C, the reaction mass is stirred up in water, suction filtered, and freed of dimethylsulfone by washing with water. After drying, 44 g of melamine is obtained, corresponding to 70% of the theoretically possible amount. An additional 8.31 g of 13% of melamine is still present in the filtrate, so that the total yield amounts to 83%. Dicyandiamide is no longer detectable in the filtrate.

EXAMPLE 6

84 g of a 50% aqueous cyanamide solution is added drop by drop to a mixture, heated at 180° C, of 140 g of dimethylsulfoxide, 2.0 g of potassium hydroxide and 1 g of solid cyanamide at such a rate that the reaction temperature of 180° C is maintained. During the 25 minutes of drop by drop addition, water and a small amount of dimethyl sulfoxide distilled out. The mixture was allowed to after-react for 10 minutes at 180° C, and then cooled. After dilution with a little water, the melamine crystals are filtered out, washed and dried. 36.4 of melamine is obtained corresponding to a yield of 84.6%. 3.82 g or 8.8% of melamine is still contained in the filtrate, so that the total yield amounts to 93.4%. In the filtrate an amount of 0.77 g or 1.8% of dicyandiamide could still be found.

EXAMPLE 7

105 g of an 80% aqueous cyanamide solution is added drop by drop to a mixture, heated at 180° C, of 280 g of dimethylsulfoxide, 3 g of potassium hydroxide and 1 g of solid cyanamide, at such a rate that the reaction temperature of 180° C is maintained. During the drop by drop addition time of approximately 30 minutes, the water distilled out along with some dimethylsulfoxide. After-reaction at 180° C is allowed for 10 minutes and the mixture is cooled. After it has been cooled to 60° C, it is distilled with water and further cooled to 20° C. After filtration and drying, 78.1 g of melamine is obtained, which corresponds to a 92% yield. In the filtrate there are still 3.15 grams of melamine or 3.7%, so that the total yield amounts to 95.7%. Furthermore, 0.8 g of dicyandiamide, or 0.95%, is still dissolved in the filtrate.

EXAMPLE 8

A solution of 63 g of solid cyanamide in 40 g of dimethylsulfoxide is added drop by drop to a mixture, heated at 180° C, of 100 g of dimethylsulfoxide and 5 g of calcium hydroxide, over a period of 12 minutes. After a post-reaction period of 10 minutes at about 180° C, the mixture is cooled. The precipitated melamine is removed by filtration, stirred up in water, and again filtered. After drying, 24.2 g or 38.4% of melamine is obtained. In the filtrate are still 6.64 grams or 10.5% of melamine. The total yield is thus 48.9%. In the filtrate there is still 43.6% (27.5 g) of dicyandiamide.

EXAMPLE 9

105 g of an 80% aqueous cyanamide solution is added drop by drop to a mixture, heated at 180PC, of 280 g of dimethylsulfoxide, 4 g of sodium hydroxide and 1 g or solid cyanamide at such a rate as to maintain the reaction temperature of 180° C. During the 30 minutes of drop by drop addition, the water distills out of the cyanamide solution together with a small amount of dimethyl sulfoxide. After cooling to 60° C, the solution is diluted with water and cooled down to 20° C. After filtration and drying, 73.8 g of melamine is obtained. Another 8 g of melamine is still dissolved in the filtrate. The total yield of melamine thus amounts to 93.2%. 0.5 g of dicyandiamide is still contained in the filtrate.

EXAMPLE 10

A solution of 83 g of solid cyanamide in 57 g of dimethylsulfoxide is added drop by drop to a mixture, heated at 160° C, of 130 g of dimethylsulfoxide, 5.2 g of potassium hydroxide and 1 g of cyanamide, over a period of 45 minutes. After another 15 minutes of reaction time at 160° C, the mixture is cooled. The precipitated melamine is filtered out, stirred up in water, and again filtered. After drying, 59 g of melamine is obtained, corresponding to 70.2%. Four grams of melamine, or 4.8%, are still dissolved in the filtrate and wash water. The total yield accordingly amounts to 75%.

EXAMPLE 11

43 g of diamide is added over a period of 40 minutes to a mixture of 187 g of dimethylsulfoxide, 10.6 g of potassium hydroxide and 1 g dicyandiamide. After another 5 minutes of reaction time at 135° C, the mixture is cooled. The precipitated melamine is suction filtered, stirred up in water, and again filtered. After drying 48.3 g of melamine is obtained, corresponding to 57.5%. In the filtrate and wash water is another 6.45 g or 7.7% of melamine in solution. The total yield is thus 65.2%.

EXAMPLE 12

A solution consisting of 3.5 g of potassium hydroxide, 1 g of crystalline cyanamide and 300 g of dimethylsulfoxide is maintained at ebullition at about 150° C by the application of a slight vacuum. 84 g of cyanamide in the form of its 80% aqueous solution is added to this mixture such that the reaction temperature of 150° C is maintained and the water is immediately distilled out, along with a small amount of dimethylsulfoxide. After the addition of the cyanamide solution is completed, the reaction mixture is maintained for another 60 minutes at 150° C, then cooled to 60° C, diluted with 200 ml of cold water, and centrifuged at 20° C. 79.7 g of very pure melamine is obtained. Another 3.7 g of melamine is still in the filtrate, so that the total yield is thus 98.2%; furthermore, the filtrate still contains 0.3 g of dicyandiamide in solution.

EXAMPLE 13

In the following series experiments the reaction was performed with aqueous 80% cyanamide solution, dimethylsulfoxide as solvent, and potassium hydroxide as catalyst. The reaction temperature was 180° C. In the first experiment the cyanamide solution was poured into the mixture of potassium hydroxide and dimethylsulfoxide, heated at 180° C. The amounts and the conditions of the reaction are stated in the following table. In the following reactions, the filtrate from the preceding experiment was reused. After adding solvent to replace losses (dimethylsulfoxide is recovered virtually without loss after distillation), the same amount of cyanamide was put in as in the first reaction, and the loss of potash lye was replaced. After each experiment the precipitated melamine was removed by centrifugation and the filtrate was reused. This primarily recovered melamine was suspended in water, filtered and dried. It is designated as "Melamine I." The melamine contained in the filtrates is designated "Melamine II."

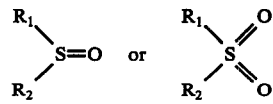

wherein
$R_1$ and $R_2$ are alkyl which may be joined together to form an alkylene ring,
in the simultaneous presence of alkali metal hydroxide or alkaline earth hydroxide.

2. Method of claim 1, wherein dimethylsulfoxide is used as solvent.

3. Method of claim 1, wherein dimethylsulfone is used as a solvent.

4. Method of claim 1, wherein sulfolan is used as solvent.

5. Method of claim 1, wherein the solvent is stabilized by the prior addition of a small amount of cyanamide and dicyandiamide.

6. Method of claim 1 wherein sodium hydroxide or potassium hydroxide is used as the alkali hydroxide.

7. Method of claim 1, wherein mixtures of alkali hydroxides are used.

8. Method of claim 1 wherein calcium hydroxide or barium hydroxide is used as the alkaline earth hydroxide.

9. Method of claim 1 wherein mixtures of alkaline earth hydroxides are used.

10. Method of claim 1, wherein cyanamide is used in the form of its aqueous solution.

11. Method of claim 1, wherein the reaction is performed under a slight vacuum.

12. Method of claim 1, wherein 0.02 to 0.2 mole of

|  | g Dimethyl-sulfoxide | g Cyanamide | g Potassium hydroxide (total) | g Filtrate | Drip-in time in min. | Post-reaction at 180° C in minutes |
|---|---|---|---|---|---|---|
| a) (1st reaction) | 1960 | 595 | 21 |  | 56 | 10 |
| b) (2nd reaction) | 830.4 | 595 | 21 | 1,129.6 | 32 | 10 |
| c) (3rd reaction) | 913.4 | 595 | 21 | 1,046.6 | 28 | 10 |
| d) (4th reaction) | 976.9 | 595 | 21 | 983.1 | 24 | 10 |

The following are the yields of melamine with respect to the cyanamid put in:

|  | Melamine I % | Melamine II % | Dicyandiamide % |
|---|---|---|---|
| a) | 87.6 | 7.0 | 0.9 |
| b) | 93 | 5.2 | 0.5 |
| c) | 95.3 | 3.7 | 0.8 |
| d) | 97.2 | 2.1 | 0.8 |

In the continuous preparation of melamine by the method of the invention, with re-use of the filtrate, the by-products did not become concentrated.

We claim:

1. Method of preparing melamine from at least one reactant selected from the group consisting of cyanamide and dicyandiamide by contacting said reactant at approximately atmospheric pressure in an organic solvent at 100° to 250° C, with at least one solvent selected from the group having the formulas alkali metal hydroxide or 0.05 to 0.5 moles of alkaline earth hydroxide are used per mole of cyanamide or dicyandiamide, respectively.

13. Method of claim 1 wherein a solution or suspension of the starting product is placed in a solution of the hydroxide preheated to reaction temperature.

14. Method of claim 1 wherein the method is performed continuously without the separation of unprecipitated melamine.

* * * * *